(12) United States Patent
Käfer

(10) Patent No.: US 6,367,473 B1
(45) Date of Patent: Apr. 9, 2002

(54) MEDIUM DISPENSER

(75) Inventor: Stefan Käfer, Eigeltingen (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 0 days.

(21) Appl. No.: 09/367,003

(22) PCT Filed: Aug. 13, 1998

(86) PCT No.: PCT/EP98/00311

§ 371 Date: Aug. 3, 1999

§ 102(e) Date: Aug. 3, 1999

(87) PCT Pub. No.: WO98/34660

PCT Pub. Date: Aug. 13, 1998

(30) Foreign Application Priority Data

Feb. 8, 1997 (DE) .......................................... 197 04 849

(51) Int. Cl.[7] .............................................. A61M 15/00
(52) U.S. Cl. ........................... 128/203.21; 128/203.12; 128/203.15; 128/203.19; 128/203.23; 604/58
(58) Field of Search ....................... 128/203.12, 203.15, 128/203.21, 203.19, 203.23; 604/58; 206/538, 532

(56) References Cited

U.S. PATENT DOCUMENTS

| | | | |
|---|---|---|---|
| 4,627,432 A | * 12/1986 | Newell et al. | 128/203.15 |
| 4,778,054 A | * 10/1988 | Newell et al. | 206/531 |
| 5,469,989 A | * 11/1995 | Graf et al. | 222/82 |
| 5,533,502 A | * 7/1996 | Piper | 128/203.21 |
| 5,584,417 A | * 12/1996 | Graf et al. | 222/82 |
| 5,740,794 A | * 4/1998 | Smith et al. | 128/203.15 |

FOREIGN PATENT DOCUMENTS

| | | |
|---|---|---|
| DE | 4021 263 A1 | 7/1990 |
| EP | 0 729 764 A1 | 2/1996 |

OTHER PUBLICATIONS

International Search Report dated Jun. 24, 1998 for PCT/EP98/00311.

\* cited by examiner

Primary Examiner—John G. Weiss
Assistant Examiner—Mital Patel
(74) Attorney, Agent, or Firm—Quarles & Brady LLP

(57) ABSTRACT

For discharging a medium, such as a powder, a film/foil seal (16) of a reservoir chamber (24) is pierced by a tool (40) in a first axial movement, after which the medium is suctioned via an orifice (9) in feeding a delivery flow via passageways (55) from the chamber (24). On completion of a return stroke and twisting the tool (40) relative to the reservoir body (6) a further chamber (24) may be emptied in the same way, thus enabling e.g. a pharmaceutical active substance to be administered in two individual doses as expedient for nasal treatment.

27 Claims, 3 Drawing Sheets

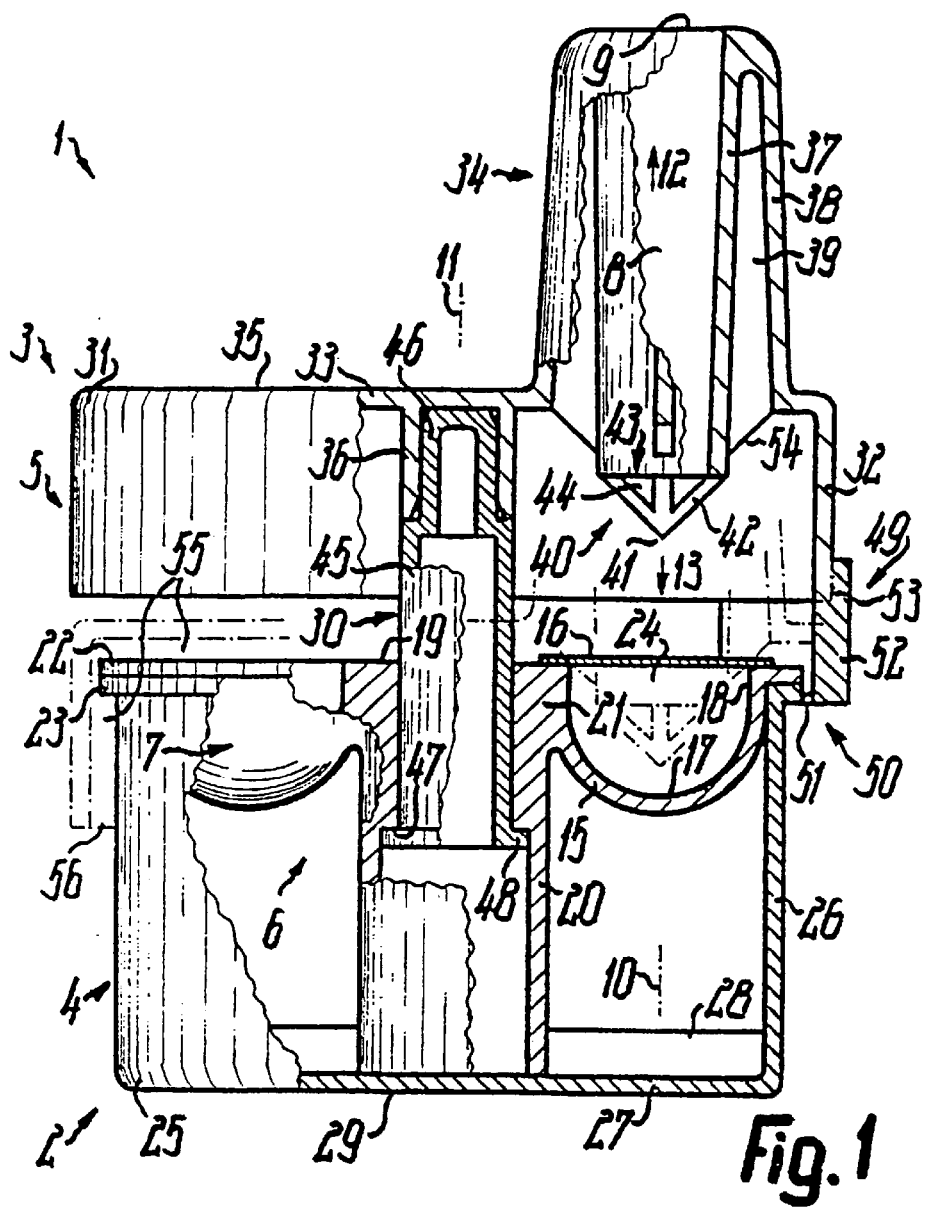
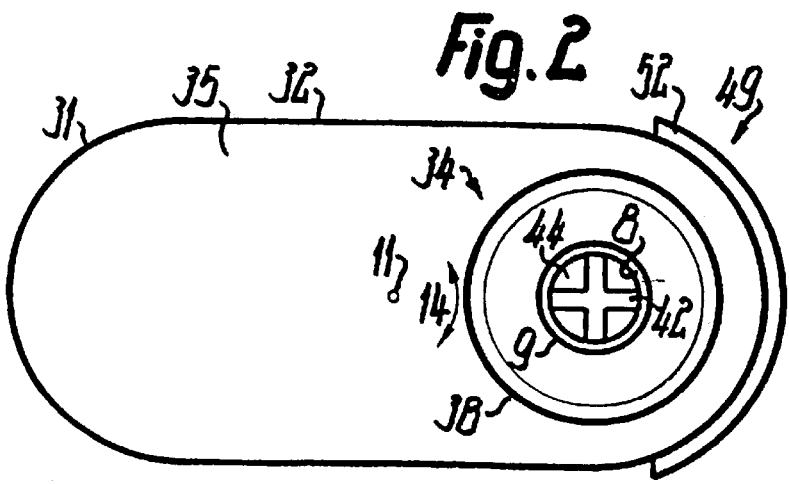

MEDIUM DISPENSER

The invention relates to a dispenser or discharge apparatus for media, more particularly for flowable media which may be gaseous, pasty or liquid, preferably powdery. Expediently in using it or in discharging the medium the dispenser is to be held or actuated single-handedly such that it is preferably suitable for suction or inhalation of the pharmaceutical active substances contained therein, so that they can be delivered e.g. to the mucous membrane of the nose. The dispenser may be made entirely of injection-molded or plastics parts.

The invention is based on the object of providing a dispenser which obviates the drawbacks of known configurations and which permits microvolume delivery by a dispenser which is simple to manufacture, assemble, handle, keep, or the like.

In accordance with the invention the individual delivery dose of the medium may be provided in a cupped or similar reservoir chamber substantially hermetically presealed so that it may be agitated as thoroughly as possible by an inlet/delivery flow on discharge of the medium to ensure the medium being emptied in one go totally from the reservoir cup exclusively through the medium orifice remote therefrom. The inlet flow may be formed by a medium of the aforementioned kind, more particularly however air, which flows into the dispenser from without, gaining access via passageways to the reservoir cup where a swirl or rotary flow is generated to mixingly entrain the medium stored therein and thus emerge as the delivery flow through the medium orifice into the atmosphere. Although the delivery flow could be generated by a pressure source or pump of the dispenser, a particularly simple configuration materializes when the inlet flow is generated by a suction flow in the outlet passage or in the reservoir cup, namely e.g. solely by the user inhaling through the medium orifice.

The reservoir chamber may comprise—like a blister pack—a cupped body and as the reservoir seal a plastics film or metal foil, or the like, secured to the face side about the reservoir opening in the reservoir body, this film/foil possibly being configured single or multi-ply and secured expediently by bonding, such as hot sealing to produce a hermetic seal to prevent the medium from gaining access between the adjacent surface areas of the reservoir body and the sealing wall from the reservoir chamber. However, the reservoir chamber may also be a pump cylinder with or without a prefitted plunger into which on actuation a finger with or without plunger enters.

Prior to discharge of the stored dose of the medium this seal is opened by being ruptured, but without destroying the bonding or seal connection, more particularly so that it is merely slitted open without any debris of the seal becoming detached, i.e. instead all parts of the seal remaining securely attached to the reservoir body after opening so that they cannot be entrained in the flow to the outlet passage. For this opening action the dispenser comprises instead of the plunger, or in addition thereto, a tool, provided preferably at the inflow end of the outlet passage and able to work in two phases in sequence. In the first phase only the center of the sealing wall is urged into the interior of the reservoir chamber until it ruptures, after which the sealing wall is slit open radially to form several radial flaps of the sealing wall which in the second phase are splayed or defined by being clamped in place relative to the reservoir body, thus ensuring that even in the case of a highly flexible sealing film/foil a sufficiently large passage cross-section for the inlet flow materializes without the risk of the seal flaps reclosing or restricting the passage cross-section once the flow action is effective.

The volume of the reservoir chamber may be several times, e.g. at least two or three times, larger than the volume of the discharge dose stored therein so that already on commencement of discharge of the medium suitably large spaces are available for developing a swirl flow and the passage inlet or the inlet openings thereof are not fully covered by the medium on plunging into the reservoir chamber. The inlet flow gains access directly to the medium expediently through an annular passage defined by the reservoir chamber and/or an outlet nozzle, whereby on leaving the annular passage the inlet flow is directed as a kind of annular roller radially inwards and then back in the opposite direction into the outlet passage. The bottom of the reservoir cup which is concave over the full width of the reservoir chamber as well as the conically tapered end of the outlet passage serve as curved or inclined guiding surface areas for the reverse flow. During discharge of the medium these guiding surface areas are defined centered and stopped relative to each other to have so little freedom of movement that the definition of the cup chamber or bottom thereof remains out of contact. The flaps of the sealing wall define the passageways for the inlet flow within the reservoir chamber, however, from the opening of the reservoir up to the region of the guiding surface areas so that their ends are free to flutter in the air flow, whirling up the medium mechanically.

The dispenser receives the reservoir cup expediently totally in a housing which may be permanently fixed or movable relative to the medium orifice. Expediently the reservoir chamber is movable relative to the medium orifice, the outlet passage, the opening tool or the like, e.g. by being shiftable parallel to the centerline of the cup or pivotable about an axis parallel to the cup centerline. This pivoting or twisting axis is located radially totally outside of the reservoir chamber so that it may be translated from a location in line with the outlet passage into a location remote therefrom. It is this axial movement that enables the reservoir seal to be opened and the rotary movement enables the reservoir cup to be translated from a resting position into an operating position, the reservoir cup being unable to come into contact with the outlet passage in the resting position when the outlet passage is axially shifted.

The dispenser may comprise on a common reservoir body two or more reservoir chambers the same or differing in size which may be translated into the operating position or discharge position in sequence by one of the cited movements and thus emptied each separately in one go. These reservoir chambers are distributed to advantage uniformly about the axis of rotation, whereby between them a supporting or mounting appendage may be provided protruding beyond the bottoms of the cups and transmitting axial actuating forces directly to the reservoir body.

To facilitate piercing the reservoir wall or actuation for discharge of the medium the parts movable relative to each other for this purpose are expediently loaded via a pressure point, after the defeat of which the forces counteracting the actuation are substantially diminished throughout up to the stop so that the dispenser may be translated at relatively high speed into the end position of the stroke. The self-releasing resistive forces of the pressure point may be formed by a spring latch, a design break point or the like. The members releasing for this purpose by interengagement or by the actuating force may be, like anti-twist members, located in the region of the outer circumference of the reservoir body or be formed by the outermost circumference thereof so that the reservoir body requires no separate appendages or the like for this purpose.

The anti-twist members, by means of which the reservoir body is prevented from twisting out of place from the inner end of the outlet passage on discharge of the medium, may act positively throughout from the starting position of the reservoir body up to the end position of the stroke whilst still being releasable, e.g. by the two actuating units of the dispenser being telescopically extensible up to the mutual stop. In this arrangement the pressure point may be defeated in the opposite direction so that the actuating units are then located in the starting position in which they are stop-defined in both opposite directions, namely against being telescopically extended by a stop which is very difficult to defeat and against being telescopically retracted by the contacting sliding surface areas of the pressure point control which is substantially easier to defeat.

The dispenser may be configured miniature, e.g. fully clasped single-handedly circumferentially or surrounded lengthwise so that the discharge nozzle freely protrudes between two fingers of the hand. Its largest radial width is maximally 60 mm or 50 mm and its length maximally twice as large as compared to the latter may be maximally 90 mm or 70 mm. These dimensions like all mutual locational definitions may apply to both the starting position as well as the end position after the dispenser has been actuated.

These and further features also read from the description and the drawings, each of the individual features being achieved by themselves or severally in the form of sub-combinations in one embodiment of the invention and in other fields and may represent advantageous aspects as well as being patentable in their own right, for which protection is sought in the present.

Example embodiments of the invention are explained in more detail in the following and illustrated in the drawings in which:

FIG. 1 is an illustration of the dispenser in accordance with the invention, shown partly in axial section.

FIG. 2 is a plan view of the dispenser as shown in FIG. 1,

Figure 1A:
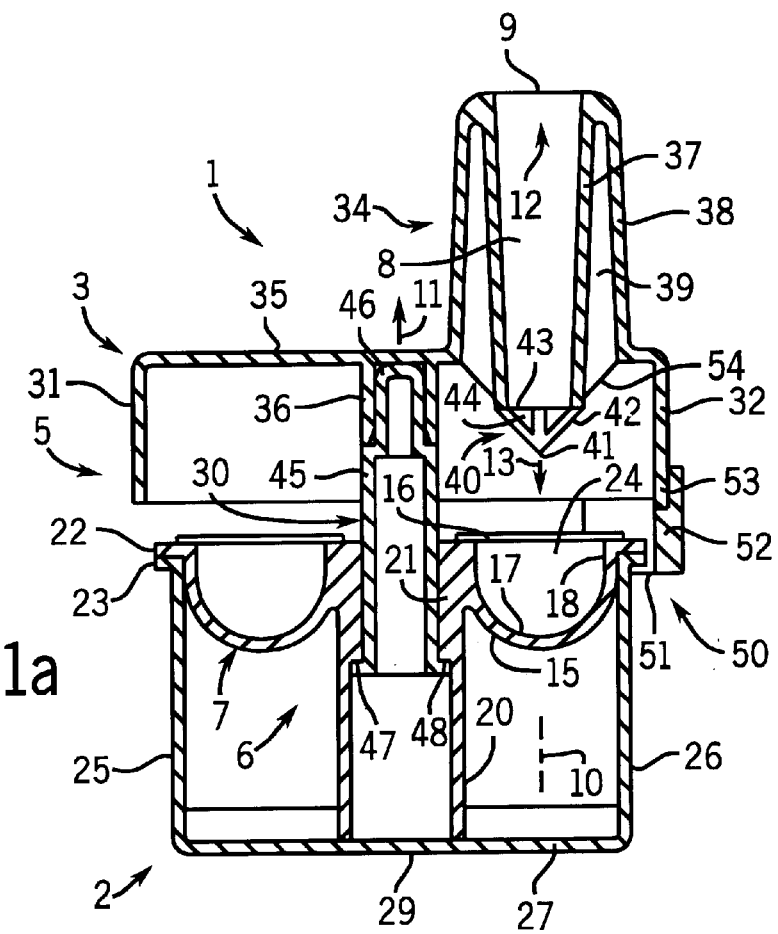
FIG. 1a is a vertical section view of the embodiment of FIG. 1 in the pre-actuation position.

The dispenser 1 comprises two units 2, 3 opposingly movable by manual actuation in two directions located at right angles transversely to each other. By linear movement the units 2, 3 are translated from a starting position or resting position with a shortening of the dispenser 1 into an actuated end position or working position as well as back into the starting position by manual force. By rotary movement the units 2, 3 are opposingly displaced into various optional positions only in the linear resting position in opposite directions through at least 180° or more than a full turn in each case. The first unit 2 located downwards on discharge of the medium comprises a bowl-type base body 4 with an internal reservoir body 6 and the second unit 3, located on top of the other unit on discharge of the medium, comprises a base body 5. Each of the base bodies 4, 5 as well as the reservoir body 6 is configured integral throughout.

The reservoir body 6 separate from the base body 4 could also be configured integral with the base body 4 and in addition the two base bodies 4, 5 could be produced integral with each other and then, without being parted from each other, translated from the mutual production position into the starting position or operating position different thereto by being turned. As a result of this the dispenser may be made exclusively of plastics material or injection molded parts without employing any metal and also requires no springs such as control or return springs. Furthermore, the dispenser may be produced miniature, e.g. comprising a length of 10, 8 or 6 cm and a width at right angles transversely thereto of 6, 5 or 4 cm smaller as compared to the latter, whereby each of the cited dimensions may be a maximum or minimum value. The dispenser may be configured for discharging only a single dose of the medium or for discharge in sequence of at least or maximally two, three or four doses of the medium located adjacent to each other in a plane at right angles and transversely to the linear displacement or axis of rotation of the units 2, 3 and contained in separate reservoirs 7. The spatial volume of each reservoir 7 is substantially larger than the volume of the medium contained therein so that the medium is moved or loosened up in the reservoir 7 by shaking.

On being discharged the medium flows from the reservoir 7 directly into an outlet passage 8 linear throughout up to a medium orifice 9, the flow cross-sections of the outlet passage continually increasing from the reservoir 7 up to the medium orifice 9. The outlet passage 8 comprises in cross-section only a single definition formed by an inner circumference and has at both ends a maximum width which is smaller than the largest inner width of the reservoir 7. On discharge of the medium as well as in the starting position previous thereto the reservoir 7 and the outlet passage 8 are located in a common axis 10 parallel to the direction of displacement, as compared to which the axis 11 parallel thereto for the rotational movement of the units 2, 3 is laterally spaced away therefrom by a spacing which is smaller than a third of the maximum width of the dispenser 1. The axis 11 forms the centerline of the dispenser 1 or of each of the units 2, 3 and an axis of symmetry for the bodies 4, 6. On being discharged the medium flows from the unit 2 through the unit 3 in the direction 12 and for translation into the actuated end position the unit 3 needs to be moved relative to the unit 2 in the opposite direction 13. For translation into the various rotary positions the units 2, 3 are opposingly twisted in the direction 14 about the axis 11. An actuated end position is indicated dot-dashed in FIG. 1. On being discharged the medium detaches from the dispenser 1 as a whole at the orifice 9.

For each reservoir 7 the reservoir body 6 comprises a separate reservoir cup 15 the plane opening of which is sealed off by a plane reservoir seal 16, namely a diaphragm, a film, foil or the like hermetically so that the reservoir cup 15 can only be opened by destroying the seal 16. The bottom wall of the cup 15 curved inwardly concave and outwardly convex forms internally a hemispherical reservoir bottom 17 which translates continually into a reservoir shell 18 constant in width up to the opening. The length of the shell 18 is substantially smaller than its width or the maximum width of the bottom 17 and may be smaller than a third or half of the radius of this width. The reservoir opening is located in a face surface area 19 of the body 6 plane throughout and located at right angles transversely to the axis 10, 11, extending up to outermost circumference of the unit 2, 4 and permanently forming the surface area of this unit 2, 4, 6 nearest to the orifice 9.

All reservoirs 7 are configured integral with a tubular supporting body 20 hollow throughout located in the axis 11, the outer circumference of which is connected by the reservoir cups 15 via separate stems 21 uniformly distributed about the axis 11, as a result of which the reservoir body 6 has differing wall thicknesses, namely smaller in the region of the reservoir cup 15, the lower end of the supporting body 20 as well as in the region of a flanged deck or a rim 22, but each the same as the other, and in the region of the stems 21 wall thicknesses which are more than twice as thick as compared to the latter. The stem 21 and the rim 22 form together the face surface area 19, the stem 21 being axially shorter than the reservoir cup 15 so that the curved bottom wall thereof protrudes downwards beyond the stem 21 and is located radially spaced away adjacently from the outer circumference of the supporting body 20.

The radial spacing of the outer circumference of the cup 15 from the axis 11 equals the radius of the freely exposed outer circumference of the supporting body 20 so that the stem 21 does not protrude beyond these outer circumferences at right angles transversely to the plane common to the axes 10, 11. In the axial view as shown in FIG. 2 the dispenser 1 just like each of its units 2, 3 or the base bodies 4, 5 is elongated or oval parallel to this axial plane so that its smallest width amounts at the most or at least to half of its maximum width and one of two reservoirs 7 is located at each end. Due to the thickened portions of stems 21 located diametrally opposed and due to the free surface area 19 being penetrated only by the reservoir openings the reservoirs 7 are connected to each other substantially flexibly rigid and to the supporting body 20. The reservoirs 7 are further stiffened by the fixed connection of the reservoir body 6 to the base body 4. The rim 22 of the face surface area 19 rests by its full circumference on the face or end surface area of the base body 4 facing the orifice 9, this face or end surface area being formed by a rim 23 of the body 4 consistent in width and thickness. The rims 22, 23 may be configured also integral with each other and surround the reservoir chambers 24 of all reservoirs 7 in the plane of the reservoir openings and of the reservoir shells 18.

The base body 4 is formed by a cap 25, configured elongated as viewed axially, which in each axial section comprises a constant inner and outer width throughout up to the rim 23 and forming a shell 26 as well as at the end thereof facing away from the orifice 9 a plane face wall 27. Each reservoir cup 15 is in contact with the inner circumference of the shell 26 in its portion furthest removed from the axis 11, namely symmetrical to the axial plane 10, 11 and directly adjoining the inner circumference of the rim 23 by half the partial circumference of its outer circumference, i.e. only up to the transition between the bottom 17 and the shell 18 so that the bottom wall of the cup 15 is located within the base body 4 totally without any contact. The rim 23 protrudes only beyond the outer circumference of the shell 26 and forms with the rim 22 about the circumference a common, smooth circumferential surface area continual throughout which dictates the largest outer width of the unit 2. The bottom 27 is located axially spaced away from the reservoir cups 15, this axial spacing being greater than its axial extent. Spaced away from the reservoir cups 15 the walls 26, 27 are mutually joined by stiffeners, such as ribs 28, adjoining only at the inner sides of the walls 26, 27 as well as at the outer circumference of the supporting body 20 extending up to the inner side of the bottom 27. The web-shaped ribs 28 located radially to the axis 11 may thus form by their end edges from each other a divided centering opening for clampingly receiving the lower end section of the supporting body 20.

When the body 6 is inserted into the body 4 it is first the supporting body 20 that engages this centering opening, after which the outer surface areas of the cups 15 located inclined to the direction of insertion 13 engage with the inner side of the shell 26 and thereby produce, where necessary, a mutual twisting alignment of the bodies 4, 6. It is solely by the engagement of the outer surface areas of the reservoir cups 15 with the inner surface area of the cap 25 that the bodies 4, 6 are then oppposingly positively and permanently prevented from twisting out of place with zero clearance. Due to the mutual stop by the rims 22, 23 and by the parts 20, 27 the bodies 4, 8 are opposingly axially locked in place permanently with zero clearance. The outer circumference of the reservoir cups 15 may also clampingly engage the inner circumference of the body 4 with radial pressure, or the rims 22, 23 may be hot-sealed or fused to each other so that any accidental parting of the bodies 4, 6 is obviated. The body 6 seals off the interior of the body 4 hermetically at its cup opening. Opposite the outer circumference of the supporting body 20 as well as the stems 21, namely in the region of its plane longitudinal sides, the inner circumference of the body 4 has no contact with the body 6 throughout since the outer width of the supporting body 20 and of the stems 21 transversely to the axial plane 10, 11 is smaller than the corresponding outer width of the cup 15. The outer side of the wall 27, plane throughout, forms a handle 29 for locating one or more fingers as well as a surface area for reliably standing the dispenser on a plane table top.

The two units 2, 4 and 3, 5 are connected to each other before or directly after commencement of the actuating movement only by a single telescopic-type connection 30 located centrally in the axis 11 and which may be configured integral with one or more of the bodies 4 to 6. In this case, however, the connection 30 exposed between the units 2, 3 in the starting position is formed by a component separate from the bodies 4 to 6 and permits their shifting movement both axially, but with zero radial clearance, as well as their mutual rotary movement. In the starting position all reservoir cups 15 are located totally outside of the body 5 and in the actuated end position totally within the body 5 beyond which then only the longitudinal part of the body 4 adjoining the reservoirs 7 with the handle 29 protrudes outwardly.

The body 5 comprises likewise an integral and, as viewed axially, elongated or oval cap 31, the shell 32 of which freely protrudes from its plane face wall 33 only in the direction of the handle 29. The inner circumference of the shell 32 is slightly wider than the outer circumference of the body 4 or of the rim 22, 23 so that the latter may be pushed into the shell 32 more or less up to the inner side of the face wall 33, passageways thereby remaining free between the inner sides of the walls 32, 33 and the outer sides of the walls 22, 23, and a wall of the shell. As suction channels these passageways connect the opened reservoir chamber 24 to the outer atmosphere surrounding the dispenser 1 and run in the direction of flow multiply angled first in the direction 12 along the outer circumference of the wall of the shell 26, 23, 22, then transversely to the axis 10, 11 along the face surface area 19 or of the seal 16 about the connection 30 and then in the direction 13 through the reservoir opening towards the reservoir bottom 17, and from there in the direction 12 they translate deflected into the outlet passage 8. These passageways may pass through the full circumference of the bodies 4, 6 without interruption so that in the actuated end position they comprise passage cross-sections larger throughout than the outlet passage 8, but form a constriction or sieve gap defined by the rims 22, 23 to prevent the intake of any foreign matter. Between the faces of rims 22, 23 the passageways form a flat passage gap extending over the full face surface area 19, this gap being penetrated centrally only by the connection 30 so that the latter is directly surrounded by the air flow.

Protruding beyond the outer side of the face wall 33 in the axis 10 is a discharge nozzle 34 configured integral with the body 5, 31. Located in the end surface area of the discharge nozzle 34 is the orifice 9 as a right circular opening having a width of at least 2, 4 or 5 mm. Adjacent to and directly connecting the outer circumference of the nozzle 34 the otherwise plane outer side of the face wall 33 forms the second handle 35 for locating one or more fingers of the same hand. Like the handle 29, the handle 35 extends full-length up to the corresponding shell 26 and 32 respectively, whereby both handles 29, 35 are penetrated by the axis 11 since the nozzle 34 is located totally adjacent to the axis 11 but spaced away therefrom. Protruding less far than the shell 32 eccentrically adjacent to the nozzle 34 only beyond the inner side of the face wall 33 is a protuberance 36 totally located within the cap 31. The sleeve-shaped insertion protuberance 36 is configured integral with the face wall 33 and forms part of the connection 30.

The double-wall nozzle 34 comprises an outermost shell 38 conically flared at an acute angle in the direction 13 up to the wall 33, this shell extending only up to the wall 33 and translating thereinto integrally. At the other end located at the orifice 9 the shell 38 translates integrally into a freely protruding inner shell 37 conically tapered at an acute angle, which from the connection with the shell 38 extending up to the orifice 9 is without contact to the shell 38 over its full length and over most of its outer circumference and thus freely protrudes in the direction 13 beyond the inner side of the wall 33 into the cap 31. The outer circumference of the shell 37 is integrally connected to the inner circumference of the shell 38 via stiffeners, such as ribs 39 which protrude from the transition between the shells 37, 38 up to the inner side of the wall 33 as well as into the cap 31. The longitudinal or axial ribs 38 are distributed uniformly about the axis 10 and set back relative to the adjacent ends of the tubular 37, 38.

The inner circumference of the tubular shell 37 defines alone the sole outlet passage 8 conically flared at an acute angle in the direction 12. The length of the nozzle 34 is smaller than the spacing between the handles 29, 35 in the resting position or in the actuated end position. The outer width of the nozzle 34 is selected closely behind its free face surface area with a 6 mm diameter so large that it may be introduced into a nostril and come into contact with the inside of the nostril relatively snugly when already inserted only slightly. The cited face surface area translates rounded into the conically outer circumference of the shell 38. Curved partly or semi-circular about the axis 10 in every working rotated position are also the shells 26, 32 as well as the rims 22, 23, whereby these curved sections as viewed axially translate into each other via straight flanking sections of the shell or rim in each case.

Figure 1B:
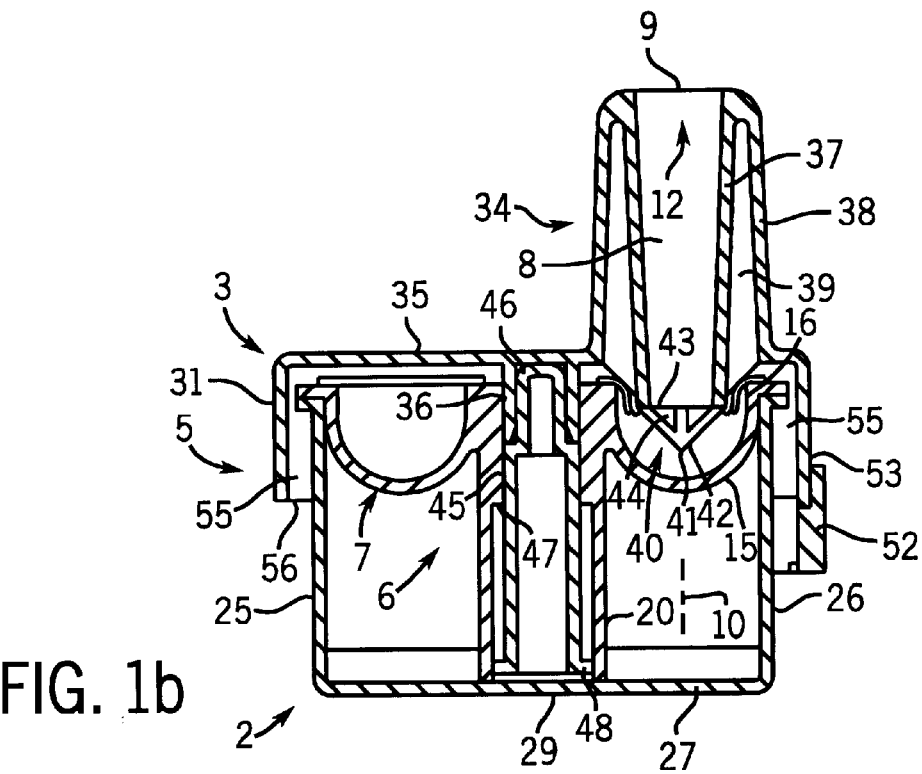
FIG. 1b is a vertical section view of the embodiment of FIG. 1 in the actuated position.

As evident from FIG. 1 a separate seal 16 is provided for each reservoir chamber 24, although an integral common seal throughout may also be provided for two or more or all reservoir chambers 24. The seal 16 is joined by hot-sealing or fusion only to the face surface area 19, beyond which it protrudes only by its thickness of maximally half or a tenth of a millimeter. To open the seal 16—which is flexible but capable of bursting without debris—of a chamber 24 located in the axis 10 of the passage 8, a tool 40 is provided on the unit 3, 5, this tool being located totally within the cap 31 at the end of the passage 8 or of the shell 37 and protruding beyond this end, as a result of which the inner shell forms a spike 37 with which the complete tool 40 is integrally configured as with the remaining body 5.

Located nearest to the sealing plane 19 in the axis 10 is a tip 41 of the tool 40 pointing in the direction 13, this tip being configured spaced away from the corresponding end of the hollow spike 37 as a 90° conically pointed tip. Integrally adjoining the tip 41 in the direction 12 are the webs 42, the ends of which remote from the tip 41 integrally adjoin the face or end surface area of the shell 37 so that they protrude in the plane of this face surface area beyond neither the inner circumference nor the outer circumference of the shell 37. The outer longitudinal edges of the four webs 42 uniformly distributed about the axis 10 form a smooth inclined continuation of the outer circumference of the tip 41 and their inner longitudinal edges diverge in the direction 12 in the same way inclined to the axis 10. The side edges of each web 42 are located parallel to each other so that, between them, triangular ports 44 of the passage inlet 43 of the passage 8 are formed in each case uniformly distributed about the axis 10. The passage cross-section of the single port 44 as well as of all ports 44 jointly is smaller than that of the passage 8, the orifice 9 and of the cited passageways for the delivery air flow, as a result of which the tool 40 forms protruding beyond the plane end surface area of the shell 37 a sieve, a flow restrictor and a swirler for the flow, the ports 44 of which are defined by the end surface area of the shell 37 as well as by the webs 42.

In the actuated end position, in which the body 5 or the shell 37 is directly stop-defined relative to the body 4 or 6, the end of the tip 41 is located away from the bottom 17 by a spacing which is smaller than the radius of curvature thereof or half thereof, whilst the end surface area of the shell 37 is located in the region of the bottom 17 or in the region of the transition between the bottom 17 and the shell 18. The outer circumference of the shell 37 then defines with the shell 18 an annular passage interrupted by the ribs 39, this annular passage starting from the reservoir opening or the face surface area 19 and pointing axially in the direction of the bottom surface area 17. At the end surface area of the shell 37 the continuation of this annular passage which is then defined by the webs 42 and the opposite bottom wall 17 first assumes a wider passage cross-section before then again becoming narrower towards the tip 41. The air flowing through the annular passage towards the surface area 17 is caused to swirl about the axis 10 by the guiding surface area 17, this swirl flow entering through the ports 44 into the passage 8 and simultaneously emerges mixed with the medium from the orifice 9.

The closed chamber 44 is filled expediently only with medium sufficient to partly cover the bottom 17 and in the working position the ports 44 dip into the medium either not at all or only in part to thus achieve a very good swirling entrainment of the medium and also size reduction of any large particles possibly formed by minute particles sticking together. When the spike 37 dives into the chamber 24 the medium is displaced radially outwards about the axis 10 by the tool 40 so that the medium fill in the center forms a depression.

In the diving action it is only the tip 41 that first comes into contact with the seal 16, causing it to be pricked before then being slit open in the further diving action by the webs 42 and the ribs 39 only along radially lines up to the shell 18 and divided into individual circular sectioned flaps. These flaps then extend only up to the surface level of the medium in the chamber 24 and are caused to radially vibrate and flutter by the inlet flow of air, resulting in the delivery flow impacting the medium to be pulsed, it also leaving the orifice 9 pulsed. Each rib 39 is located with a tool member 42 on the same side of the axis 10 in a common axial plane and translates into this member 42 graduated about the outer circumference of the shell 32.

The connection 30 comprises but a single connecting member 45 separate from the bodies 4 to 6, namely an arbor connected to the body 5 firmly seated axially and prevented from twisting out of place. A tapered end of the hollow member 45 configured rotationally symmetrical full-length and located in the axis 11 is inserted as a connector spigot 46 firmly seated in the protuberance 36 so that the outer circumference of this connecting member smoothly adjoins the outer circumference of the cylindrical connecting member 45 the same in width. In the starting position the member 45 passes through a gap between the end surface area of the cap 31 and the rim 22, 23. As of the surface area 19 the outer circumference of the member 45 engages the inner circumference of the arbor 20 shiftingly, rotatively as well as sealed so that a telescopic connection materializes. Provided spaced away below the cups 15 and above the wall 27 on the inner circumference of the boss 20 is a stop 47 formed by the annular shoulder at the transition to a flared inner cross-section of the arbor 20, pointing away from the body 5 and forming together with the counter-stop 48 of the member 45 a captive lock for the units 2, 3 in the starting position. The counter-stop 48 is formed by a widened annular collar at the outer circumference and end of the section of the member 45 which is guided up to the counter-stop 48 slidingly on the body 6. In the actuated end position the member 45 with the counter-stop 48 comes up against the inner side of the wall 27. In this end position the ribs 39 may still feature a gap spaced away from the annular defining edge of the shell 18 and of the reservoir opening respectively.

Prior to first-time use (priming) the two units 3, 4 are joined together by a tamper-proof seal 49 safeguarding the bodies 4, 5 in the starting position or in an intermediate position and sealing off the gap between the bodies 4, 5 over part or all of the circumference from the atmosphere. The seal 49 can be translated into the release position needed to permit the formerly blocked actuating movement and rotary mutual movement of the units 2, 3 only by destroying a connection 51, namely its connection to the body 4 and/or the body 5. The cupped seal tag 52 is in this case curved about the axis 10 of the passage 8 and of the tool 40, located symmetrical to the axial plane 10, 11 and extending about the axis 10 at an angle of an arc of less than 180° and more than 90°. The seal tag adjoins the ends of the shells 26, 32 facing each other, it possibly translating via a design break connection integrally into the shell 32, as indicated by the dot-dashed line 53, and being configured separately from the body 5 so that it may form at the inner circumference centering and stop surface areas for both the outer circumference and the end edge of the shell 32. The member 52 is integrally connected to the outer circumference of the rim 23 by the connection 51 protruding inwardly from the inner circumference of the member 52 and adjoining the lower end surface areas of the rim 23 the same as of the member 52.

In joint integral fabrication of the bodies 4, 5 the connection 51 could be configured as a film hinge-type joint so that both bodies 4. 5 may be produced located juxtaposed in cap openings facing in the same directly before then being folded together about the hinging axis into the position as shown in FIG. 1. The connection 51 may be released either by applying strong axial pressure to the handles 29, 35 or by manual peeling off the seal tag 52 radially outwards by it being flexurally deformed and totally removed from the two bodies 4, 5.

In the first case as cited the member 52 remains on the base body 5 so that although mutual axial movement of the units 2, 3 is still permitted, their mutual rotation about the axis 11 is not, due to the remaining member 52 preventing this. As soon as on the axial stroke the rim 22, 23 is attained in the shell 32 this too prevents any rotational movement of the units 2, 3 irrespective of the seal 49 since the inner circumference of the member 52 forms a smooth continuation of the inner circumference of the shell 32. It is not until the units 2, 3 have been telescopically extended into their starting position that it is possible to dislodge the member 52 in destroying the connection 51 by mutually twisting the bodies 4, 5 and thus permit the rotative movement needed to align the passage 8 with the second reservoir 7.

To facilitate opening the chamber 24 a pressure point control 50 is provided which locks the units 2, 3 in place until a predetermined pressure force is attained at the surface areas 29, 35, it then being easily defeated so that the units 2, 3 are able to be manually urged towards each other greatly accelerated and only the seal 16 of the selected chamber 24 is pierced. In this case the holding member of the pressure point control is to be viewed as being the connection 51 which, however, after destruction is no longer effective for discharge from the second reservoir 7. In order to have an effective pressure point control 50 on opening or discharging each reservoir 7, the units 2, 3 could be arranged to interengage in the starting position via a radially pliant latch which is disengaged on actuation and reengaged on the return to the starting position. Apart from being effective between the outer and inner cross-section of the bodies 4, 5 the latch could also be effective directly between the bodies 5, 6, e.g. by providing a protruding latch cam on the supporting part 20 adjacent to the lower end surface area of the members 45, 48.

The nozzle 34 may be introduced into the bodily opening of a patient being treated before or after the axial actuation. In the first case a pump for boosting the delivery flow into the chamber 24 as well as into the passage 8 could be provided and formed e.g. by the member 45, 48 acting as the plunger and the body 6, 20 as the barrel. In the case as illustrated, however, the dispenser 1 is totally valveless since an inlet valve or an outlet valve is needed in none of the passageways for the delivery flow and the medium. After axial actuation the end edges 54 of the ribs 39—provided converging at an acute angle in the direction 12 with the axis 10, namely oriented parallel to the webs 42 and in a linear elongation from their inner edges—are located axial slightly spaced away from the sharp defining edge of the chamber opening flanked at right angles in the axial section so that these edges 54 protrude up into the shell 18.

Located between the outer sides of the bodies 4, 6 and the inner sides of the body 5 are the portings or passageways 55 as explained extending from the full circumference of the shells 26, 32 between the parallel rims 22, 23 up to the full circumference of the spike 37 and from there directly onto the chamber 24. The outer width of the spike 37 is greater than two-thirds of the inner width of the shell 18 and the mean width of the passage 8 corresponds to half the width of the shell 18. When air is suctioned through the orifice 9 from the passage 8 and the chamber 24 without an intervening valve, then air flows via the passageways 55 from without via an inlet 56 in the way as described and likewise without valve control into the chamber 24 so that the medium is strongly swirled therein and then the resulting, well homogenized mixture of medium and delivery flow forced out in sequence through the ports 44, the passage 8 and the orifice 9. Once the chamber 24 has been emptied the units 2, 3 are manually returned from the end position in which the member 45, 48 is stopped in contact with the bottom 27 back into the stopped extended starting position so that their mutual anti-twist lock is now released. The units 2, 3 are then counter-twisted about the axis 11 through 180° so that the parts 34, 37 to 44, 54 are then aligned on the second reservoir 7 still to be opened. This can then be emptied into the second nostril by axial actuation in the way as described.

Figure 3:
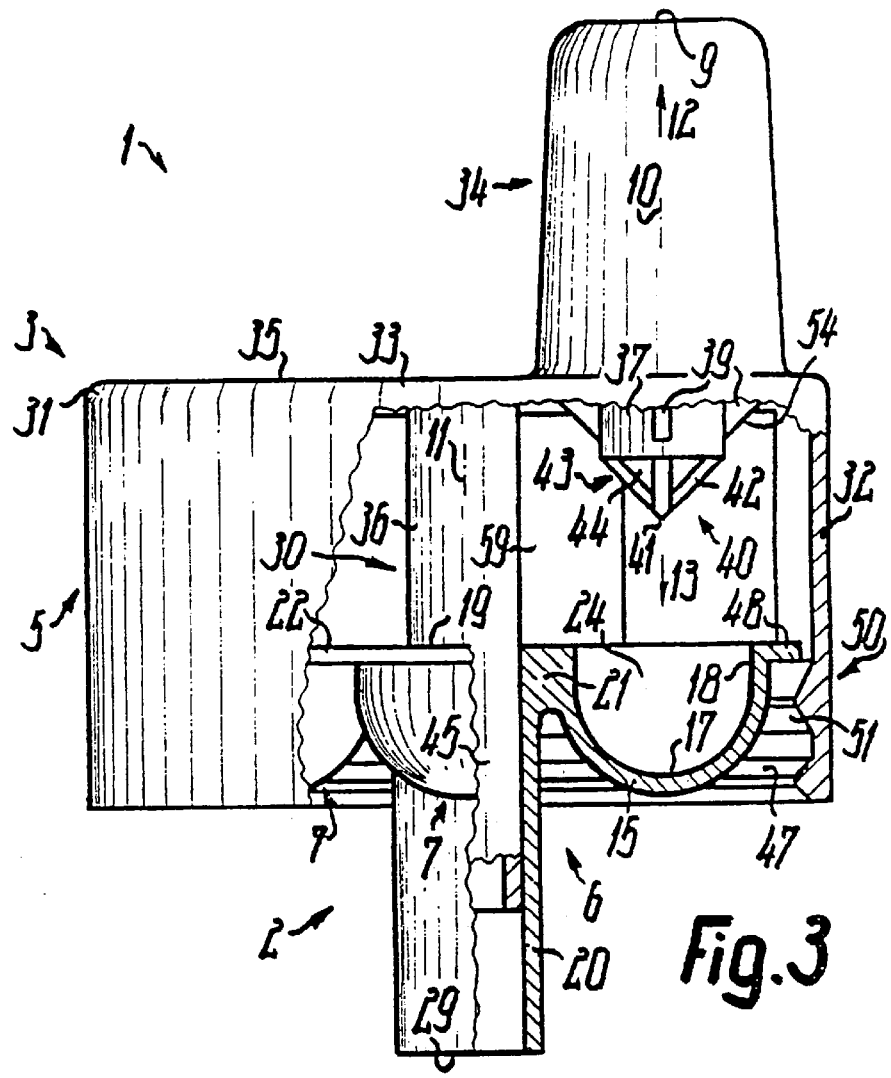
FIG. 3 is an illustration of a further embodiment shown the same as in FIG. 1.

In the case as shown in FIG. 1 the axial extent of the shank 34 is greater than the axial extent of the cap 31, whereas in the case as shown in FIG. 3 it is smaller, but smaller than the axial extent of the body 4 and 6 respectively. The axial stroke is smaller than the axial extent of each of the caps 25, 31 or of the nozzle 34, the length of which corresponds to the spacing between the handles 29, 35 in the actuated end position. The cap 31 is half as short as the cap 25 which accommodates the cap in its interior only in the actuated end position, the length of the cap 31 being measured from the face surface area 35 up to the end edge of the shell 32. The axial extent of the body 6 equals that of the cap 25 or of the body 4 as a whole, thus resulting in the dispenser 1 being configured miniature and simple to operate.

For assembly, first the member 45, 48 is inserted from below in the direction 12 into the supporting part 20 until it comes up against the stop 47, it then being connected to the body 5 via the protuberance 36 and spigot 36, 46 in the same direction of insertion 12. Then, this assembly is inserted in the direction 13 into the body 4, the cap 32 at 53 comes up against the lock 49 resulting in the dispenser 1 then being ready for priming as described. If the member 45, 48 is to form an assembly with the body 5 prior to being fitted to the body 6, for example, due to it being configured integral with the body 5, the member 48 could be configured as a snap-action member or the like which on insertion in the direction 13 into the supporting part 20 deflects from the face surface area 19 initially radially inwardly before snapping back radially outwards into its locking position after having negotiated the shoulder 47.

The annular space defined by the outer circumference of the supporting part 20, the inner circumference of the shell 26, the inner side of the wall 27 as well as by the walls of the reservoir cup 15 and between adjacent cups 15 by the inner side of the flanged deck 22 is vacant, i.e. free of fixed installed items so that reservoir cups 15 differing in depth may be inserted in one and the same cap 25. Since the magnitude of the stroke is dictated solely by the reservoir body 6 or by its cooperation with the counter-stop 48, adapting the stroke to the corresponding cup depth is simply done by making changes to the reservoir body 6 as well as to the connecting member 45 without involving any change to the bodies 4, 5. In any case, however, the reservoir cups are located spaced away from and between the handles 29, 35 in each actuation position.

Figure 4:
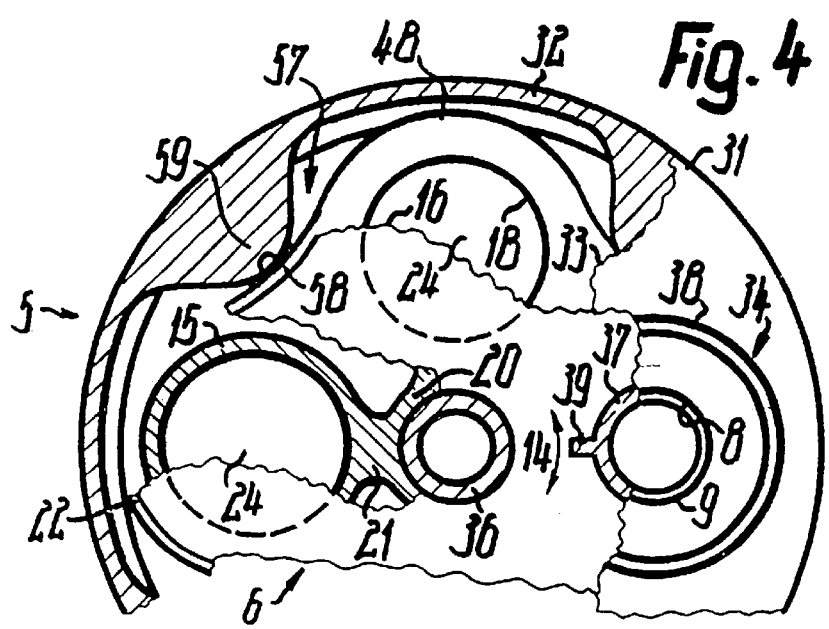
FIG. 4 is a partly sectioned plan view of the dispenser as shown in FIG. 3.

As evident from FIGS. 3 and 4 the body 4 may be eliminated altogether or be formed solely by the body 6, 20 forming with the lower end of the supporting part 20 also the handle 29. In this case the protuberance 36 is configured integral with the remaining connecting member 45. In the starting position too, all reservoirs 7 or cups 15 are located totally within the shell 32, beyond the lower opening of which only the supporting part 20 freely protrudes. The arrangement may be made so that on the actuating stroke the member 45 emerges slightly from the lower end 29 of the shank 20 before the tip 41 has attained the seal 16, the user then feeling the corresponding relative location between the units 2, 3 by his finger pressing against the handle 29. The four chambers 24 or cups 15 uniformly distributed about the axis 11 are connected to the shank 20 via the stems 21 so that although the stems 21 translate directly into the rim 22 they are located spaced away from each other circumferentially, as a result of which each cup 15 is able to execute a slight, resilient pivoting movement relative to the shank 20 like a single-armed and radial lever freely protruding from the shank 20.

In this case the interengaging members of the control 50 are provided directly at the bodies 5, 6, namely at the inner circumference of the shell 32 and at the outermost circumference of the rim 22 as well as being configured each integral with the corresponding body 5 and 6 respectively. Adjoiningly the rim 22 comprises at its free end edge surface areas 47, 51 opposite each other which may be provided full-length as the flanks of an annular groove about the axis 11. Both surface areas 47, 51 are formed by separate radial protuberances each defined by two flanks. The flank 47 of the protuberance located nearer to the end edge of the shell 32 exerts a greater return resistance on the protuberance 48 of the body 6 than the corresponding flank of the protuberance belonging to the shoulder 51 and may be located e.g. at right angles to the axis 11. The rim 22 forms around each cup 15 a most prominent radially rim protuberance 48, the surface areas 47, 51 being located in the movement travel of all protuberances 48. In the starting position the protuberances 48 are located expediently between the surface areas 47, 51 so that on actuation the inclined surface area 51 first needs to be slidingly overcome by the protuberances 48 with the cited resilient definition of the body 6 before the accelerated working stroke commences. Then, when the units 2, 3 are telescopically re-extended, the body 6 deforms correspondingly in the opposite direction when the protuberances 48 slide along the other inclined surface areas of the protuberance of the surface area 51 into the region of the latching opening 47, 51. In the starting position the body 6 is accordingly locked in place by a snap-action connection of the control 50.

In each working rotary position the two units 2, 3 are positively prevented from being twisted mutually out of place by a lock 57, but with sufficient rotary play to permit a slight, mutual resilient twisting movement to permit their precise mutual alignment in axial stopping of the surface area 54 at the unit 2. Between two protuberances 48, each defined as viewed axially semi-circular and convex, the outer end surface area of the rim 22 forms in each case a semi-circular and concave definition recess 58 engaged by a protuberance 59 at the inner circumference of the shell 32 with slight radial tension with the cited rotary play. The protuberance 59 guides the body 6 practically over the full actuating stroke, but releases it for the rotative movement about the axis 11 when the latching members 48 are located in the latching opening 47, 51. In this arrangement latching members are also provided expediently in the region of the groove 47, 51 which may be defeated, unlike the lock 57, by the manual rotary force exerted on the body 6 and which always locks in place when a chamber 24 is located in the axis 10. From this latching position effective solely by positive friction the body 6 is then translated into the positive rotary lock 57 directly on commencement of the working stroke. For this purpose the end surface area of the protuberance 59 is able to approach the axis 11 inclined in the direction 12. In the region of each protuberance 59 the thickness of the shell 32 may be reduced so that it forms at the outer circumference a finger scallop for the user.

The dispenser 1 described is particularly suitable for powdered, grainy or similar, flowable media or solid substances. However, it may be just as suitable for liquid or pasty media, the part 40 or part 16 then comprising a plunger sliding sealed along the shell 18 to thus produce a discharging pressure in the chamber 24. The tool 40 for opening or piercing the plunger or seal 16 may also be a hollow needle of a metallic material, more particularly stainless steel, through which the outlet passage 8 is guided. In this case the outlet passage 8 is then expediently guided through an outlet valve which does not open until a sufficiently high pressure has built up in the chamber 24 due to the travel of the stroke. In this configuration the delivery flow may also port directly into the passage 8, the orifice 9 of which is formed expediently by an atomizer nozzle with means for swirling the medium. As evident from FIGS. 3 and 4 the units 2, 3 or the bodies 5, 6, but especially the cap shell 32, are defined circular about the axis 11 as viewed axially so that the handles 29, 35 do not extend longitudinal transversely to the axis 10, 11 as shown in FIGS. 1 and 2.

It will be appreciated that all features of all embodiments are interchangeable or supplementary to each other for any one dispenser, so that all passages of the description apply to all embodiments. All cited effects and properties such as locational definitions, size relationships or the like may be provided precisely as described, or merely substantially or approximately so and may also greatly deviate therefrom depending on the required discharge effect.

What is claimed is:

1. A dispenser having two bodies which are rotatable relative to one another, one of said bodies, being a base body, comprising a discharge nozzle having a piercing element which has an inlet and outlet for a medium to be inhaled through the nozzle and another of said bodies, being a reservoir body, comprising multiple sealed reservoirs for containing the medicament which when pierced by the piercing element the medium will flow from the inlet of the piercing element to the outlet and out an orifice.

2. The dispenser according to claim 1, wherein said reservoirs comprise a reservoir being concavely bounded by a reservoir cup, and wherein an outlet shell bounds said outlet.

3. The dispenser according to claim 2, wherein said reservoir chamber is bounded by a substantially wherein said reservoir chamber is bounded by a substantially hemispherical cup bottom.

4. The dispenser according to claim 1, wherein while extracting the medium said reservoir bounds a substantially annular inlet opening for passing inlet flow into said reservoir.

5. The dispenser according to claim 4, wherein said outlet is located inside the piercing element, said reservoir being bounded by a cup bottom opposing a cup aperture, and an annular duct connecting said cup aperture with said cup bottom, said annular duct being coaxial with said inlet of said piercing element.

6. The dispenser according to claim 1, wherein said reservoir is bounded by a cup wall and a reservoir closure including a closure wall thinner than said cup wall, said closure wall being bonded to a cup rim and hermetically sealing said reservoir while being releasable only by being destroyed, said reservoir closure being substantially planar.

7. The dispenser according to claim 1, wherein actuating means are included for opening said reservoir by a manual actuating motion.

8. The dispenser according to claim 1, and further including abutment means, wherein while discharging the medium said outlet is positively locked relative to said reservoir by said abutment means while simultaneously an inclined face engages a recess of said reservoir containing body.

9. The dispenser according to claim 1, wherein said outlet is surrounded by longitudinal ribs circumferentially subdividing said reservoir and including front edges which substantially connect to said reservoir body when manually actuating said dispenser.

10. The dispenser according to claim 1, wherein a piercing element is included for opening said reservoir, said piercing element being located in the vicinity of said inlet and covering said outlet when viewed in axial view, for opening said reservoir said piercing element substantially exclusively slitting said reservoir body, ports of said inlet being inclined relative to an axis of said reservoir.

11. The dispenser according to claim 1, wherein said base body includes said piercing element including a plunger and said inlet, while discharging the medium said plunger extending inside said reservoir and being spaced from a cup bottom of said reservoir, wherein passageways extend within said reservoir from a constriction into a widened section adjoining said cup bottom.

12. The dispenser according to claim 11, wherein said piercing element and said reservoir commonly provide a mixing and swirl chamber for a delivery flow radially inwardly deflected in said reservoir over an angle of substantially 180° into said outlet.

13. The dispenser according to claim 1, wherein said reservoir is bounded by a reservoir cup supported substantially exclusively circumferentially by said base body and including a cup aperture, said reservoir cup including a rim enveloping said cup aperture.

14. The dispenser according to claim 13, wherein said reservoir cup includes a cup shell and said reservoir body includes a support body, said cup shell eccentrically connecting to said support body substantially in one part.

15. The dispenser according to claim 1, wherein said at least one base body includes a first base body and a second base body manually displaceable relative to said first base body, said first base body supporting said reservoir and said second base body including said outlet, while discharging the medium said first and second base bodies being interconnected substantially exclusively via said reservoir body.

16. The dispenser according to claim 15, wherein said reservoir body is mounted on said second base body directly adjacent to said reservoir via a telescopic mount, while discharging the medium said reservoir body being located substantially entirely within at least one of said first and second base bodies and radially adjacent to said telescopic mount.

17. The dispenser according to claim 1, wherein control means are included for manually overcoming a pressure resistance while initially actuating said dispenser.

18. The dispenser according to claim 17, wherein said at least one base body includes first and second base bodies, said control means including means for locking said second base body relative to said first base body in an initial position, said control means including a rated rupture connection interconnecting said first and second base bodies, a captive lock being included for preventing said second base body from being withdrawn from said first base body.

19. The dispenser according to claim 1, wherein said reservoir body includes a plurality of individual reservoirs each of said individual reservoirs, being individually connectable to said outlet.

20. The dispenser according to claim 1, wherein said base body includes a first base body and a second base body manually axially and rotatably displaceable relative to said first base body, an arbor being included and rotatably engaging said reservoir body.

21. The dispenser according to claim 1, wherein said base body is a cap and includes a cap shell prevented from rotating relative to said reservoir body by rotation prevention means, at least while discharging the medium said rotation prevention means being located in the vicinity of said cap shell.

22. The dispenser according to claim 21, wherein said rotation prevention means include a positioning member located on an outer circumference of said reservoir body and on an inner circumference of said cap shell, said rotation prevention means including means for axially slidingly displacing said cap shell relative to said reservoir body.

23. The dispenser according to claim 1, wherein said base body includes said outlet duct and a discharge nozzle, said discharge nozzle including a free end traversed by said medium outlet said discharge nozzle including first and second shells commonly bounding said medium outlet, said first shell being nested inside said second shell and radially spaced from said second shell, said first shell defining a length extension different from a length extension of said second shell, said first shell freely protruding into said base body.

24. The dispenser according to claim 1, wherein said reservoir body and base body include peripheral faces located outside of said at least one reservoir, passageways being bounded by said peripheral faces.

25. The dispenser according to claim 24, wherein said base body includes a cup end wall including an inner face, said reservoir body including an end face opposing said inner face, said end face and said inner face commonly bounding said passageways.

26. The dispenser according to claim 24, wherein said base body includes a first cap shell, and a second cap shell enveloping said first cap shell, said passageways ending upstream in an inlet and suction opening substantially circumferentially bounded by at least one of said first and second cap shells.

27. A dispenser according to claim 1, wherein said base body being rotatable around an axis of rotation, said sealed reservoirs being disposable near said piercing element by rotation and then pierced by movement of said base body in direction of said axis.

* * * * *

UNITED STATES PATENT AND TRADEMARK OFFICE
CERTIFICATE OF CORRECTION

PATENT NO.     : 6,367,473 B1
DATED          : April 9, 2002
INVENTOR(S)    : Stefan Käfer It is certified that error appears in the above-identified patent and that said Letters Patent is hereby corrected as shown below:

Column 3,
Line 58, "body 4" should be -- body 2 --.

Column 5,
Line 23, "free" should be -- face --.

Column 6,
Line 48, "shell." should be -- shell 26 --.
Line 53, "26,23" should be -- 26 and rims 23 --.

Column 7,
Line 35, "37," should be -- shells 37, --.

Column 11,
Line 25, "spigot 36, 46" should be -- spigot 46 --.

Signed and Sealed this

Twenty-sixth Day of November, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO.     : 6,367,473 B1
DATED          : April 9, 2002
INVENTOR(S)    : Stefan Kafer It is certified that error appears in the above-identified patent and that said Letters Patent is hereby corrected as shown below:

<u>Title page,</u>
Item [22], "PCT Filed: Aug. 13, 1998" should read -- PCT Filed: Jan. 21, 1998 --.

Signed and Sealed this

Thirteenth Day of April, 2004

JON W. DUDAS
*Acting Director of the United States Patent and Trademark Office*